United States Patent [19]

Meguriya et al.

[11] Patent Number: 5,068,380
[45] Date of Patent: Nov. 26, 1991

[54] ANIONIC SILICONE SURFACTANT AND METHOD OF ITS MANUFACTURE

[75] Inventors: Noriyuki Meguriya; Syuuichi Azechi; Masaki Tanaka, all of Gunma, Japan

[73] Assignee: Shin-Etsu Chemical Co., Ltd., Tokyo, Japan

[21] Appl. No.: 450,492

[22] Filed: Dec. 14, 1989

[30] Foreign Application Priority Data

Dec. 15, 1988 [JP] Japan ............... 63-316656

[51] Int. Cl.$^5$ .................. C07F 7/08; C07F 7/10
[52] U.S. Cl. ........................ 556/428; 556/413
[58] Field of Search .................. 556/428, 413

[56] References Cited

U.S. PATENT DOCUMENTS 4,717,498  1/1988  Maxon ........................ 556/428 X
4,777,277  10/1988  Colas et al. ................. 556/428 X
4,814,471  3/1989  Renauld ...................... 556/428

Primary Examiner—Paul F. Shaver
Attorney, Agent, or Firm—Millen, White & Zelano

[57] ABSTRACT

An anionic silicone surfactant, with excellent surface tension lowering properties in aqueous and solvent systems, of the general formula

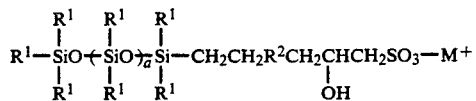

wherein each $R^1$ is an unsubstituted or halogen-substituted monovalent hydrocarbon group of 1-20 carbon atoms or a trialkylsiloxy group of 1-20 carbon atoms; $R^2$ is an unsubstituted, halogen-substituted or hydroxyl-substituted bivalent hydrocarbon group of 1-10 carbon atoms, or a corresponding hydrocarbon group wherein no more than half of the carbon atoms are replaced by an oxygen atom; M is a Group A alkali metal or $NR^3R^4R^5$ wherein $R^3$, $R^4$ and $R^5$ are a hydrogen atom or a monovalent hydrocarbon group of 1-20 carbon atoms; and $a$ is a number which lies in the range $0 \leq a \leq 20$, is produced by reacting a corresponding organopolysiloxane which is terminated at one end by a silicon atom bearing a hydrogen atom with a compound of the general formula

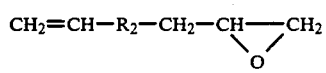

in the presence of a platinum catalyst, and reacting the thus-produced epoxy group-terminated organopolysiloxane with sodium or potassium bisulfite.

9 Claims, No Drawings

ANIONIC SILICONE SURFACTANT AND METHOD OF ITS MANUFACTURE

FIELD OF THE INVENTION

This invention relates to an anionic silicone surfactant and a manufacturing method thereof.

BACKGROUND OF THE INVENTION

Silicone surfactants have been reported in the literature. See for example the non-ionic organopolysiloxane surfactants described by Maki and Komori in the journal "Kagaku Kogyo", Vol. 73, No. 6, and in the journal "Hyomen", Vol. 7, No. 11. They are known to be much more effective in lowering surface tension than hydrocarbon surfactants.

As these substances are non-ionic, however, they are of the polyether type. Their dimethylpolysiloxane chain is therefore comparatively short, and their range of application is consequently limited.

Cationic and anionic organopolysiloxane surfactants are also known. See Japanese Patent Kokoku ("Examined Japanese Patent Publication") No. 49-11760. These substances, however, were mixtures of polymers with functional groups at both ends and polymers with functional groups on side chains, or mixtures wherein polymers with functional groups at only one end had been added to the former mixtures, and as a result, these substances did not exhibit good surfactant properties.

In order to widen the range of application of silicone surfactants, therefore, it was necessary to further develop ionic silicone surfactants.

The inventors of this invention carried out intensive research with a view to providing a solution to this problem. Then, using a siloxane which was reactive at one end as starting material to synthesize a surfactant, it was found that an anionic silicone surfactant with extremely good surface tension lowering properties could be obtained, which this led to the present invention.

SUMMARY OF THE INVENTION

The first object of this invention, therefore, is to provide an anionic silicone surfactant with excellent surface tension lowering properties.

A second object of this invention is to provide a method of manufacturing an anionic silicone surfactant with excellent surface tension lowering properties.

The above objects of the present invention are attained by an anionic silicone surfactant represented by the general formula (I), and by the method of manufacturing it herein described,

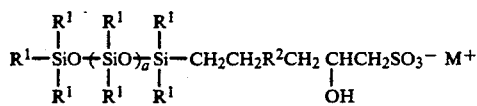

wherein $R^1$, $R^2$, M, and "$a$" have the values given hereinafter.

The surfactant of this invention has an effect which is due to the low surface tension of siloxane itself. In addition, as a siloxane with a reactive group at one end is used as starting material, the product is an AB type block copolymer which is an ideal structure as a surfactant. The product therefore exhibits excellent surface tension lowering properties in aqueous systems or solvent systems. It is not only excellent as a foaming agent, penetrating agent or cleaner, but due to the affinity of the siloxane fragment for silicone oil, it also performs very well in the form of a silicone oil emulsion.

DETAILED DESCRIPTION OF THE INVENTION

In the general formula (I), the $R^1$ groups are unsubstituted or halogen-substituted monovalent hydrocarbon groups of 1–20 carbon atoms, wherein the $R^1$ groups can be identical to or different from one another. The monovalent hydrocarbon groups denoted by $R^1$ may for example be alkyl groups such as methyl, ethyl, propyl, butyl, pentyl, hexyl, octyl or dodecyl; aryl groups such as phenyl, tolyl, benzyl, and naphthyl; or monovalent hydrocarbon groups of the above type which have been substituted by hydroxyl or halogen atoms such as fluorine, chlorine and bromine. It is in particular preferable that no less than 80% of the $R^1$ groups are methyl. $R^2$ is an unsubstituted, halogen-substituted or hydroxyl-substituted bivalent hydrocarbon group of 1–10 carbon atoms, and may for example be an alkylene group such as methylene, ethylene and propylene, a corresponding bivalent aromatic group such as phenylene, or a bivalent group substituted by halogens or hydroxyl.

Further, no more than ½ of the carbon atoms in $R^2$ may be substituted by oxygen; M is a Group A alkali metal or $NR^3R^4R^5$ ($R^3$, $R^4$ and $R^5$ being respectively hydrogen atoms or monovalent hydrocarbon groups of 1–20 carbon atoms, wherein $R^3$, $R^4$ and $R^5$ can be identical to or different from one another. Further, a is a number which lies in the range $0 \leq a \leq 20$.

The surfactant of this invention represented by general formula (I) is obtained by reacting an organopolysiloxane with an Si—H bond at one end represented by the formula:

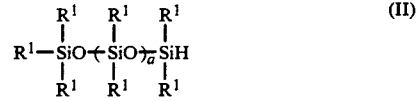

with a compound of general formula:

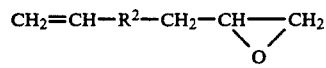

in the presence of a platinum catalyst so as to obtain an organopolysiloxane represented by the formula:

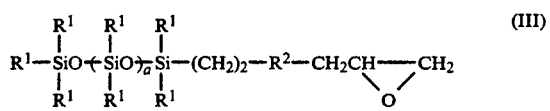

and then reacting this organopolysiloxane with a bisulfite of a monovalent metal such as sodium bisulfite or potassium bisulfite. In Formulae II and III, $R^1$, $R^2$, "$a$", and M have the values given above.

In this case, a compound of general formula (II) may be obtained by reacting a hexaorganocyclotrisiloxane with a triorganosilanol in the presence of, for example, a penta-coordinated silicon compound catalyst represented by the formula:

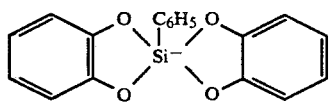

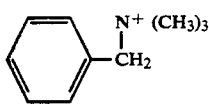

to give an organopolysiloxane terminated by a silanol group at one end represented by the formula:

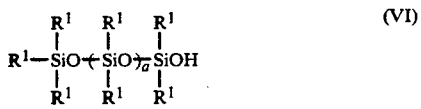

and then removing hydrochloric acid from a reaction mixture of the resulting polymer and a diorganochlorosilane of the type [H(R$^1$)$_2$SiCl] by means of a dehydrochlorinating agent such as, for example, trimethylamine. Further, if [H(R$^1$)SiCl$_2$] is used as the chlorosilane, a product with a side chain can also be obtained. In these formulae also, R$^1$ and "$a$" have the values given above.

The organopolysiloxane thus obtained not only retains the effect of the low surface tension of siloxane itself, but also, as a reactive siloxane at one end is used as the starting material, the product is an AB type block copolymer which has an ideal structure as a surfactant. As a result, the organopolysiloxane of this invention exhibits excellent surface tension lowering properties in both aqueous systems and solvent systems. It may therefore be used as a foaming agent, penetrating agent or cleaner, and as the siloxane fragment has an affinity for silicone oil, it also performs very well in the form of a silicone oil emulsion.

EXAMPLES

We shall now describe the invention in more detail with reference to specific examples. It should however be understood that the invention is in no way limited to these examples.

EXAMPLE 1

90 g of trimethylsilanol, 50 g of toluene and 120 g of triethylamine were introduced successively into a three-necked flask of capacity 1 l equipped with a thermometer, stirrer and reflux condenser. 94.5 g of dimethyl-mono-chlorosilane were then dripped in at room temperature with stirring, and stirring was continued for 3 hours. After washing the reaction mixture obtained with water, a siloxane represented by the formula:

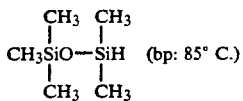

was obtained by distillation.

200 g of the siloxane thus obtained, 300 g of toluene, 169 g of an epoxy compound represented by the formula:

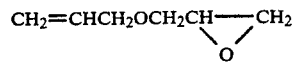

and 0.1 g of a 2% isopropanol solution of platinic acid chloride (H$_2$PtCl$_6$. 6H$_2$O) were introduced into a three-necked flask of capacity 1 l similar to the above, and the mixture was heated at 70° C.-90° C. for 5 hours. After verifying that the absorption of the Si—H bond (2150 cm$^{-1}$) had disappeared on the IR spectrum of the reaction mixture, the solvent was distilled off from the reaction mixture under reduced pressure so as to obtain a clear liquid. This liquid was analyzed by gas chromatography, and found to be 97% pure with 280 epoxy equivalents (calculated value 262). It was thus verified that the liquid was an epoxysiloxane represented by the following structural formula:

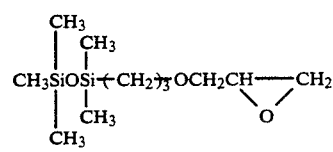

262 g of the epoxysiloxane obtained above, 260 g of ethanol and 26 g of water were then introduced into a similar flask to the above, and the mixture was heated to 80°-85° C. After heating, a saturated aqueous solution of 133 g sodium bisulfite (NaHSO$_3$) and 6.25 g of sodium sulfite (Na$_2$SO$_3$) was dripped in over a period of about 1 hour, and stirring was continued at 85° C. for 10 hours. After completion of the reaction, the temperature was raised to 95° C., ethanol was distilled off, 300 g of toluene were added, and then water was distilled off. After filtering off solids, the residue was extracted with methanol to give 230 g of a solid having the following formula:

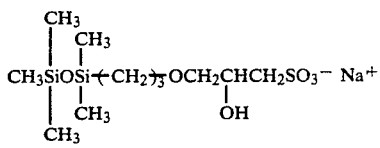

The product obtained was soluble in water, and after carrying out ion exchange, a neutralization titration showed that it contained 95% of the theoretical quantity of —SO$_3$H.

An elemental analysis was carried out. The calculated values were: C: 36.1%, H: 7.8%, Na: 6.3%, Si: 15.3%. The experimental values were: C: 37.0%, H: 7.5%, Na: 5.9% and Si: 16.2%.

It is seen that the experimental values agree well with the calculated values (% indicates weight per cent).

The compound thus obtained will hereafter be referred to as Surfactant A.

EXAMPLE 2

666 g of hexamethylcyclo-trisiloxane, 90 g of trimethylsilanol and 0.1 g of the penta-coordinated silicon compound catalyst with the structural formula given in this specification were introduced into a three-necked flask of capacity 1 l equipped with a thermometer, stirrer and reflux condenser, and reacted together at 80° C. with stirring for 16 hours to synthesize a siloxane terminated by a silanol group at one end which is represented by the formula:

$$\text{CH}_3\text{SiO}\text{-}(\text{SiO})_{78}\text{SiOH}$$
with CH$_3$ groups on each Si.

60 g of trimethylamine and 94.5 g of dimethylmonochlorosilane were then dripped into the above obtained reaction mixture at room temperature with stirring, and stirring was continued for 5 hours. After washing the reaction mixture obtained with water, a liquid polysiloxane represented by the formula:

$$\text{CH}_3\text{SiO}\text{-}(\text{SiO})_{78}\text{SiH}$$
with CH$_3$ groups on each Si.

was obtained.

As in Example 1, this was reacted in the presence of a platinum catalyst with the epoxy compound:

$$CH_2=CHCH_2OCH_2CH\underset{O}{\overset{}{\diagdown\diagup}}CH_2$$

so as to obtain an epoxysiloxane. The epoxysiloxane obtained was reacted with sodium bisulfite to obtain a brown liquid represented by the formula:

$$\text{CH}_3\text{SiO}\text{-}(\text{SiO})_{78}\text{Si}\text{-}(\text{CH}_2)_3\text{OCH}_2\text{CHCH}_2\text{SO}_3^- \text{Na}^+$$
with CH$_3$ on Si and OH on CH.

This brown liquid was insoluble in water, but soluble in ethylene glycol and methanol. After ion exchange, a neutralization titration showed that it contained 92% of the theoretical quantity of —SO$_3$H.

An elemental analysis was carried out. The calculated values were: C: 33.7%, H: 7.8%, Na: 2.2%, Si: 29.8%. The experimental values were: C: 35.1%, H: 7.9%, Na: 2.0% and Si: 29.0%.

It is seen that the experimental values agree well with the calculated values (% indicates weight per cent).

The compound thus obtained will hereafter be referred to as Surfactant B.

EXAMPLE 3

The surface tension lowering capacities of Surfactant A and Surfactant B obtained in Examples 1 and 2, were measured with a Counter Balance Vertical Plate surface tension meter. As B was not water-soluble, however, ethylene glycol solvent was used. In this measurement, $C_{12}H_{25}OSO_3Na^+$ (surfactant C) was used as a comparison sample.

The results are shown in Table 1.

TABLE 1

| Surface Tension Change by various surfactants | | | | | |
|---|---|---|---|---|---|
| concentration (mol/l) | $10^{-5}$ | $10^{-4}$ | $10^{-3}$ | $10^{-2}$ | $10^{-1}$ |
| (aqueous system) | | | | | |
| Surfactant A | 65.1 | 40.1 | 21.3 | 20.9 | 20.4 |
| Surfactant C | 71.5 | 56.2 | 41.7 | 38.3 | 36.5 |
| (Ethylene glycol system) | | | | | |
| Surfactant B | 42.9 | 38.5 | 32.1 | 29.9 | 28.0 |
| Surfactant C | 45.1 | 44.7 | 43.9 | 43.1 | 42.5 |

From the results in Table 1, it is proved that the surfactants of this invention have far greater surface tension lowering capacity than conventional hydrocarbon anionic surfactant.

What is claimed is:

1. An anionic silicone surfactant represented by the formula $$R^1-\underset{R^1}{\overset{R^1}{\text{SiO}}}\text{-}(\underset{R^1}{\overset{R^1}{\text{SiO}}})_a\underset{R^1}{\overset{R^1}{\text{Si}}}-CH_2CH_2R^2CH_2\underset{OH}{\overset{}{C}}HCH_2SO_3-M^+$$

wherein each $R^1$ is an unsubstituted or halogen-substituted monovalent hydrocarbon group of 1-20 carbon atoms or a trialkylsiloxy group of 1-20 carbon atoms; $R^2$ is an unsubstituted, halogen-substituted or hydroxyl-substituted bivalent hydrocarbon group of 1-10 carbon atoms, or a corresponding hydrocarbon group wherein no more than ½ of the carbon atoms are replaced by an oxygen atom; M is a Group A alkali metal or $NR^3R^4R^5$, wherein $R^3$, $R^4$ and $R^5$ are a hydrogen atom or a monovalent hydrocarbon group of 1-20 carbon atoms; and $a$ is a number which lies in the range $0 \leq a \leq 20$.

2. The anionic silicone surfactant of claim 1, wherein no less than 80% of the $R^1$ groups are methyl groups.

3. The anionic silicon surfactant of claim 1, wherein all of the $R^1$ groups are methyl groups.

4. The anionic silicone surfactant of claim 1, wherein $R^2$ is —CH$_2$O—.

5. The anionic silicone surfactant of claim 1, wherein $R^2$ is propyleneoxy.

6. The anionic silicon surfactant of claim 1, wherein $a$ is a number from 0 to 9.

7. The anionic silicon surfactant of claim 1, wherein "M+" is Na+.

8. The anionic silicon surfactant of claim 1, wherein all of the $R^1$ groups are methyl groups, wherein $R^2$ is propyleneoxy or —CH$_2$O—, wherein $a$ is a number from 0 to 9, and wherein "M+" is Na+.

9. A method of manufacturing an anionic silicone surfactant wherein an organohydrogen polysiloxane with an Si—H bond at one end is reacted with an epoxy compound with one ethylenic unsaturated bond and one epoxy group in the presence of a platinum catalyst so as to obtain an organopolysiloxane with an epoxy group at the end, and the organopolysiloxane obtained is then reacted with a bisulfite of a monovalent metal.

* * * * *